(12) United States Patent
Aoyama et al.

(10) Patent No.: US 6,251,442 B1
(45) Date of Patent: Jun. 26, 2001

(54) FEED COMPOSITION FOR BROILERS AND METHOD FOR BREEDING BROILERS

(75) Inventors: Tomoya Aoyama; Yasuaki Sugimoto, both of Tokyo (JP)

(73) Assignee: Idemitsu Petrochemical Co., Ltd., Tokyo (JP)

( * ) Notice: Subject to any disclaimer, the term of this patent is extended or adjusted under 35 U.S.C. 154(b) by 0 days.

(21) Appl. No.: 09/423,603

(22) PCT Filed: May 14, 1998

(86) PCT No.: PCT/JP98/02120

§ 371 Date: Nov. 12, 1999

§ 102(e) Date: Nov. 12, 1999

(87) PCT Pub. No.: WO98/51164

PCT Pub. Date: Nov. 19, 1998

(30) Foreign Application Priority Data

May 14, 1997 (JP) .................................................. 9-123985

(51) Int. Cl.[7] .............................. A23K 1/16; A23K 1/18; A23K 1/165
(52) U.S. Cl. .............................. 426/2; 426/630; 426/635; 426/807
(58) Field of Search ............................... 426/2, 807, 630, 426/635

(56) References Cited

U.S. PATENT DOCUMENTS 5,951,998 * 9/1999 Aoyama et al. ...................... 424/442

FOREIGN PATENT DOCUMENTS

| 918409 | * | 2/1963 | (GB) . |
| 6231684 | * | 7/1987 | (JP) . |
| 87031684 | * | 7/1987 | (JP) . |
| 6287136 | * | 10/1994 | (JP) . |
| 07123928 | * | 5/1995 | (JP) . |
| 7123928 | * | 5/1995 | (JP) . |
| 9422433 | * | 10/1994 | (WO) . |

* cited by examiner

*Primary Examiner*—Chhaya D. Sayala
(74) *Attorney, Agent, or Firm*—Oblon, Spivak, McClelland, Maier & Neustadt, P.C.

(57) ABSTRACT

Coenzyme Q is added to a feed composition for broilers, preferably in an amount of from 0.0005 to 0.003% by weight of the total amount of the composition, and the composition is controlled to have a metabolizable energy value of not smaller than 3150 kcal/kg. The coenzyme Q-containing composition is pelletized into pellets. This is fed to broilers for 7 days or longer while the broilers being fed therewith are of 10 to 35-days age. Feeding broilers with the pelletized, coenzyme Q-containing feed composition provided by the invention makes it possible to well prevent the broilers from having ascites and to increase the growth rate of the broilers, whereby raising rate of the broilers is increased and the rearing period thereof is shortened. According to the feeding method of the invention, the productivity in broiler raising is much increased.

8 Claims, No Drawings

FEED COMPOSITION FOR BROILERS AND METHOD FOR BREEDING BROILERS

TECHNICAL FIELD

The present invention relates to a feed composition and a feeding method for broilers, precisely, to a feed composition for broilers which is effective in raising broilers both for improving the growth rate and for lowering the death rate, and also to a feeding method for broilers where is used the composition to attain high productivity.

BACKGROUND ART

In the broiler industry for raising poultry, precisely chickens, and especially broilers, improvements and developments have been made essentially in the breeding technique for phyletic lines of broilers and in the rearing technique for increasing the growth rate of broilers. Above all, much emphasis is put on the growth rate and the feed conversion rate in the method of rearing broilers, and high-calorie feed and pellet-like feed have become used for rearing broilers. Use of such feed has made it possible to increase the growth rate and the feeding efficiency, but on the other hand, has brought about some problems. Specifically, too much increase in the growth rate of broilers during the rearing period could not be followed by sufficient body metabolic functions such as the cardiac function, etc., and the imbalance therebetween has increased the death rate, thereby lowering the raising rate and the productivity to cause great economic damage to the broiler industry.

One essential cause of death of broilers from the imbalance between the growth rate and the development of cardiac functions is ascites. Broilers having been fed with high-calorie feed could grow rapidly, but it is known that, in those, the incidence of ascites is high. In addition, depending on the raising condition, many broilers often have ascites in winter or at highlands, or in raising with high stocking density of chicks.

To lower the incidence of ascites in broilers, a raising method may be taken for well controlling the growth rate to thereby make the development of the cardiac function and the growth rate balanced, which, however, is not favorable from the economic viewpoint.

Some techniques of using coenzyme Q have been developed for the means of preventing broiler ascites while keeping a high growth rate of broilers in some degree, two of which mentioned below are known.

I. Quinones containing coenzyme Q are administered to broilers to prevent them from having ascites, thereby increasing the raising rate (Japanese Patent Application Laid-Open (JP-A) Hei-6-287136).

II. Feed containing coenzymes $Q_9$ and $Q_{10}$ is used to prevent ascites and sudden death syndrome (JP-A Hei-7-123928)

They say that, in the proposed techniques, coenzymes $Q_9$ and $Q_{10}$ are effective for preventing ascites, but no sufficient discussions have been made for further increasing the growth rate of broilers according to those techniques.

In other words, no attempt has heretofore been made at using coenzyme Q for preventing ascites of broilers while keeping a suitable raising rate so as to improve the growth rate, for example, by fully analyzing the growing process of broilers to thereby design a suitable feed composition and a suitable feeding method that indicate the combination of feed and coenzyme Q to be fed to broilers with respect to the degree of metabolizable energy to be derived from the feed and to the stage at which the coenzyme Q-containing feed shall be applied to broilers during the rearing period.

The present invention has been made from the viewpoint noted above, and its object is to provide a feed composition for broilers with which broilers being fed can be fully prevented from having ascites and can grow rapidly, and which therefore makes it possible to increase the growth rate of broilers and to shorten the growing period thereof, and also to provide a feeding method for broilers where is used the composition to attain high productivity.

The term "raising rate" as referred to herein indicates the ratio of the number of the living broilers counted at the end of the rearing period to the number of all broilers in the initial stage (=number of all broilers in the initial stage−number of broilers died during the rearing period).

DISCLOSURE OF THE INVENTION

We, the present inventors have assiduously studied so as to solve the problems noted above, and, as a result, have found that when broilers are fed with a feed composition as prepared by adding coenzyme Q to feed, of which the metabolizable energy value is not smaller than a specific value, followed by pelletizing it into pellets, then it is possible to well prevent the broilers from having ascites, thereby increasing the raising rate of the broilers and increasing the growth rate thereof to shorten the period for rearing the broilers, and that when the feed composition is fed to broilers for a period of predetermined days or longer during the former stage of the rearing period, then the productivity of broilers is more effectively increased. On the basis of these findings, we have completed the present invention.

Specifically, the invention is a feed composition for broilers, which has a metabolizable energy value of not smaller than 3150 kcal/kg and contains coenzyme Q and which has been pelletized into pellets.

The metabolizable energy as referred to herein is obtained by subtracting the amount of energy as discharged in feces and urine (waste calorie) from the amount of total energy of the intake feed (total calorie), and ordinary calorimetry may be applied to each feed composition to actually obtain the metabolizable energy of the composition. In general, the metabolizable energy value of feed for chickens is obtained on the basis of known tables of calorie components for it, and such known tables may be employed herein to obtain the metabolizable energy in question.

The coenzyme Q content of the feed composition for broilers of the invention may be concretely from 0.0005 to 0.003% by weight or so of the total amount of the composition.

The invention further provides a feeding method for broilers, comprising feeding the feed composition of the invention noted above to broilers for 7 days or longer while the broilers being fed therewith are of 10 to 35-days age.

BEST MODES OF CARRYING OUT THE INVENTION

Now, the invention is described in detail hereinunder. First mentioned is the feed composition for broilers of the invention.

(1) Feed Composition for Broilers of the Invention:

The feed composition for broilers of the invention is characterized by having a metabolizable energy value of not smaller than 3150 kcal/kg and containing coenzyme Q and by having been pelletized into pellets.

The coenzyme Q to be used in the feed composition for broilers of the invention is not specifically defined, and may be any and every compound to be in the group of coenzyme Q. Concretely, it includes, for example, coenzyme $Q_6$, coenzyme $Q_7$, coenzyme $Q_8$, coenzyme $Q_9$, coenzyme $Q_{10}$, and also reduced (quinol-type) coenzyme Q of these. Of the coenzyme Q of those types, coenzyme $Q_9$ and coenzyme $Q_{10}$ are preferably used in the invention.

It is known that coenzyme Q of the types noted above exists in many animals and vegetables. As its sources, for example, known are mold fungi such as Mucor and Mortierella; yeast such as Candida and Saccharomyces; bacteria such as Pseudomonas, Achromobacter, and Rhodopseudomonas; leaves of tobacco; germs of corn and wheat, etc. Coenzyme Q can be obtained from those sources through ordinary extraction and purification. To prepare the feed composition for broilers of the invention that contains such coenzyme Q, a pure (or purified) product of coenzyme Q as obtained in the manner mentioned above may be added to feed, or alternatively, the extract or crude product as obtained from any of those sources, or even the source itself, if having a sufficiently high coenzyme Q content, may be added to feed.

Commercial products of coenzyme Q as produced through chemical synthesis are available, and any of those are employable in the invention. Also employable herein are compositions comprising coenzyme Q and any other chemicals, diluents, carriers, vehicles, etc.

Concretely, the coenzyme Q content of the feed composition for broilers of the invention is preferably from about 0.0005 to 0.003% by weight or so, more preferably from about 0.0005 to 0.002% by weight or so of the total amount of the composition. As so mentioned above, the feed composition of the invention may contain a mixture containing coenzyme Q, except for pure coenzyme Q. In this case, the mixture may be added to feed in such an amount that the coenzyme Q content of the resulting feed composition may fall within the defined range.

The feed composition for broilers of the invention comprises coenzyme Q, and may additionally contain any other optional components that are generally used in ordinary feed compositions for broilers in such an amount that the feed composition containing such optional components may have a metabolizable energy value of not smaller than 3150 kcal/kg.

The optional components usable in the feed composition for broilers of the invention include, for example, nutrient components such as corn, milo, bean-cake, vegetable oil, fish meal, rice bran, wheat bran, wheat, corn pre-meal, etc.; mineral components such as salt, shell, egg-shell, calcium carbonate, calcium secondary phosphate, etc.; vitamin agents such as vitamin ADE agent, vitamin B agent, etc.; antibiotics such as salinomycin, enramycin, etc.; various feed additive components such as choline chloride, etc.

The feed composition for broilers of the invention contains coenzyme Q within the range defined above, and may contain various optional components noted above thereby to have a metabolizable energy value of not smaller than 3150 kcal/kg. The metabolizable energy value of the feed composition can be easily controlled, for example, by increasing or decreasing the proportion of high-calorie components of the nutrient components mentioned above, such as vegetable oil, to be added to the composition. For the calorie of those nutrient components, referred to are Tables of Standard Feed Ingredients of Japan.

The metabolizable energy of the feed composition thus prepared can be obtained according to the indexing method described in "Tables of Standard Feed Ingredients of Japan, 1995" (pages 268 to 269) or in "Poultry Dietetics, written by M. L. Scott, M. C. Nesheim & R. J. Young, translated and edited by Iwao Tasaki, published by Yoken-do Co., 1983" (pages 552 to 553), in which is used chromium oxide ($Cr_2O_3$) to determine the metabolizable energy of feed to chickens. According to this method, dry feed is tested to determine various data of the feed, from which is obtained the metabolizable energy (ME) of the dry feed according to the following equation.

ME in 1 g of dry feed=GE in 1 g of dry feed−(GE in 1 g of dry feces×chromium oxide % in 1 g of dry feed/chromium oxide % in 1 g of dry feces)−8.22×cumulative nitrogen, g, per gram of dry feed ME: metabolizable energy (kcal/g)

GE: gross energy (kcal/g)

On the basis of the water content of the feed composition, the metabolizable energy (ME) of the feed is calculated according to the following equation:

ME of feed=ME of dry feed×(100−water content (%) of feed)/100

In the manner mentioned above, the metabolizable energy value of feed can be obtained according to the indexing method of using chromium oxide ($Cr_2O_3$).

The metabolizable energy to be obtained in the equations noted above is represented by a unit of kcal/g. In the present specification, however, the metabolizable energy is represented by a unit of kcal/kg.

The feed composition for broilers of the invention is further characterized in that it is in the form of pellets. The hardness of the pellets of the composition is not specifically defined, and may be the same as that of pellets of any ordinary feed composition for broilers. The shape and the size of the pellets are not also specifically defined, provided that broilers can easily take the pellets. Regarding the shape, concretely, it is desirable that the pellets are spherical, hollow macaroni-like or oval-spherical ones, or even pseudo-spherical ones of which at least one of the vertical cross-section and the horizontal cross-section is oval. Regarding the size of the pellets capable of being taken easily by broilers, the spherical, pseudo-spherical or hollow macaroni-like ones may be such that their widthwise cross-section has a major diameter of from 1 to 5 mm or so, but preferably from 2 to 4 mm or so; and the pseudo-spherical and hollow macaroni-like ones may have a length of from 2 to 15 mm or so. The size of the pellets having any other shape than those mentioned above may also be nearly the same as that noted above.

To produce the feed composition for broilers of the invention, a suitable amount of coenzyme Q is uniformly mixed with suitable amounts of components as so selected from the above-mentioned optional components that the resulting feed composition may have a metabolizable energy value of not smaller than 3150 kcal/kg, to give a feed mixture, which is then pelletized into pellets.

To pelletize the mixture into pellets, employable is any ordinary method for producing feed pellets for broilers. For example, the feed mixture prepared as above is put into a commercially-available pelletizer (manufactured by CPMCo.), and pelletized therein at a suitable temperature of around 80° C. or so to give pellets having a desired shape and a desired hardness.

To feed the feed composition for broilers of the invention thus obtained in the manner mentioned above, employable is any ordinary feeding method using ordinary feed. Where broilers are fed with the feed composition of the invention in an ordinary feeding manner, the dose of coenzyme Q to broilers, which shall be calculated from the ordinary feed intake of broilers and from the coenzyme Q content of the composition, may be generally from 0.1 to 6 mg/kg-body weight/day or so, but preferably from 0.2 to 5 mg/kg-body weight/day or so.

The feed composition for broilers of the invention has a metabolizable energy value of not smaller than 3150 kcal/kg, and is in the form of pellets that ensure efficient feed intake. Therefore, the feed composition is highly effective for increasing the growth rate of broilers fed therewith. In addition, since the feed composition contains coenzyme Q and since the dose of coenzyme Q noted above can be taken by broilers fed with the composition, it is possible to satisfactorily prevent the broilers being fed with the composition from suffering from ascites to be caused by high-calorie feed intake, in the growing stage of the broilers. Accordingly, feeding broilers with the feed composition of the invention makes it possible to increase the raising rate of the broilers and to shorten the growing period thereof, thereby effectively increasing the productivity of the broilers.

The feed composition of the invention may be fed to broilers anytime throughout the rearing period, but, if desired, broilers may be fed with the feed composition of the invention and ordinary feed alternately at predetermined intervals. In particular, preferred is the feeding method for broilers of the invention to be mentioned below, in which is used the feed composition of the invention to effectively increase the productivity of the broilers fed therewith.

(2) Feeding Method for Broilers of the Invention:

In the feeding method for broilers of the invention, used is the feed composition of the invention mentioned hereinabove to effectively increase the productivity of the broilers fed therewith. The feeding method is characterized in that broilers are fed with the feed composition of the invention noted above, for 7 days or longer while they are of 10 to 35-days age.

In the feeding method of the invention, the feed composition of the invention noted above is fed to broilers in such a manner that the feeding period from the start to the end of the feeding of the feed composition of the invention falls within the growing period of the broilers to be of from 10-days age to 35-days age. Thus, it is desirable that the feeding period is within the growing period of from 10-days age to 35-days age, but preferably within the growing period of from 15-days age to 28-days age.

In the feeding method of the invention, the feed composition is fed to broilers for 7 days or longer, but more preferably, continuously for 14 days or longer to further increase the productivity of the broilers being fed with the composition.

In the feeding method of the invention, as so mentioned above, the feed composition of the invention is fed to broilers for 7 days or longer, which concretely means that broilers of being in a free intake condition or restricted intake condition are fed with only the feed composition of the invention for 7 days or longer in total within the predetermined growing period of time for the broilers. More concretely, for example, a feeding mode of feeding broilers with the feed composition for one day at three-day intervals and for 7 days in total, while the broilers are of from 10-days age to 35-days age, is within the scope of the feeding method of the invention; and a feeding mode of feeding broilers with the feed composition continuously for 7 days, while the broilers are of the defined age period, for example, of from 15-days age to 21-days age, is also within the scope of the feeding method of the invention.

According to the feeding method of the invention noted above, the feed composition of the invention is more effectively fed to broilers to thereby more effectively increase the raising rate of the broilers and more effectively shorten the growing period thereof, whereby the productivity of the broilers being fed with the feed composition is much more increased.

The species of broiler chickens to which the feed composition and the feeding method of the invention are applied are not specifically defined. The feed composition and the feeding method of the invention are applicable to any other chickens except those for broilers, such as hens being raised for collecting eggs therefrom.

EXAMPLES

Examples of the invention are mentioned below. Coenzyme $Q_{10}$ used in the following Examples is a commercial product of coenzyme $Q_{10}$ produced by Wako Pure Chemicals Co. (chemical name: ubiquinone-10, having a coenzyme $Q_{10}$ content of 99%).

Examples 1 to 5

Feed Compositions (1) Preparation of Feed Samples:

The components shown in Table 1 were uniformly mixed to prepare feed samples a to e. The last row in Table 1 indicates the metabolizable energy value of each sample (mean value derived from n=5) having been measured according to the indexing method described in the "Tables of Standard Feed Ingredients of Japan, 1995" noted above, where was used chromium oxide, and the crude protein content thereof having been calculated on the basis of the Tables of Standard Feed Ingredients of Japan noted above.

TABLE 1

| Components | Amount (g/feed sample kg) Feed Sample | | | | |
| --- | --- | --- | --- | --- | --- |
| | a | b | c | d | e |
| Corn | 477 | 503 | 503 | 503 | 503 |
| Milo | 100 | 153 | 153 | 153 | 153 |
| Bean-cake | 248 | 169 | 169 | 169 | 169 |
| Vegetable Oil | 28 | — | 11 | 30 | 45 |
| Fish Meal | 90 | 90 | 90 | 90 | 90 |
| Wheat Bran | 13 | 24 | 24 | 24 | 24 |
| Corncob Meal | 18 | 45 | 34 | 15 | — |
| Vitamins, Minerals | 26 | 16 | 16 | 16 | 16 |
| Crude Protein Content (%) | 19 | 17 | 17 | 17 | 17 |
| Metabolizable Energy Value (kcal/kg) | 3012 | 2890 | 2995 | 3168 | 3305 |

In Table 1 above, the vitamins and the minerals were so controlled that each feed sample containing them could satisfy the nutrition requirements described in "Nutrition Requirements of Poultry, 9th Rev. Ed. (1994)" issued by NRC (National Research Council, USA), published by National Academy Press (Washington D.C.)).

(2) Preparation of Feed Compositions:

Coenzyme $Q_{10}$ was diluted with wheat bran to prepare a diluted coenzyme mixture having a coenzyme concentration of 1%. Then, the diluted coenzyme mixture was added to and well mixed with each of the feed samples d and e prepared above, to make the resulting mixtures each have the coenzyme $Q_{10}$ concentration shown in Table 2. The resulting mixtures were separately put into a pelletizing machine (manufactured by CPM Co.), and pelletized therein at 80° C. to obtain feed compositions. The pellets formed were hollow macaroni-like ones of from 3 to 6 mm long, of which the cross section was circular and had a diameter of around 2 to 3 mm or so.

For comparison, the diluted coenzyme mixture was added to and well mixed with each of the feed samples a to c, to make the resulting mixtures each have the coenzyme $Q_{10}$ concentration shown in Table 2, and pelletized in the same manner as above to obtain feed compositions. These are comparative feed compositions containing coenzyme Q but having a metabolizable energy value of lower than 3150 kcal/kg. Also for comparison, the feed sample d was well mixed with the diluted coenzyme mixture to have a coenzyme $Q_{10}$ content of 15 ppm, and then ground, using a grinder, into a mashed feed composition.

Apart from those, prepared were palletized or mashed feed compositions not containing coenzyme Q, as in Production Examples in Table 2.

The feed compositions thus obtained in those Examples, Comparative Examples and Production Examples are referred to as their code names shown in the most right-handed column in Table 2. For the feed compositions, hereinunder used are the thus-indicated codes. The details of the codes of the feed compositions are as follows: The alphabet indicates the type of the feed sample; the number to follow the alphabet via the hyphen indicates the coenzyme $Q_{10}$ content (ppm); and (M), if any, to follow the number indicates "mashed". Those with no (M) are pelletized samples.

TABLE 2

|  | Feed Sample | Coenzyme $Q_{10}$ Content (ppm) | Shape | Code |
|---|---|---|---|---|
| Example 1 | d | 5 | pellet | D-5 |
| Example 2 | d | 10 | pellet | D-10 |
| Example 3 | d | 15 | pellet | D-15 |
| Example 4 | d | 20 | pellet | D-20 |
| Example 5 | e | 30 | pellet | E-30 |
| Comparative Example 1 | a | 10 | pellet | A-10 |
| Comparative Example 2 | a | 20 | pellet | A-20 |
| Comparative Example 3 | b | 20 | pellet | B-20 |
| Comparative Example 4 | c | 30 | pellet | C-30 |
| Comparative Example 5 | d | 15 | mash | D-15(M) |
| Production Example 1 | a | — | pellet | A |
| Production Example 2 | b | — | pellet | B |
| Production Example 3 | c | — | pellet | C |
| Production Example 4 | d | — | pellet | D |
| Production Example 5 | d | — | mash | D(M) |

The feed compositions prepared above were used in the following Examples of various feeding methods for broilers.

Examples 6 to 9

Feeding Methods for Broilers

Plural groups of day-old broiler chicks (breed: Ross (male), day-old, mean body weight of 40 g), each group being composed of 50 birds, were fed with each of the feed compositions prepared above, in a floor feeding manner, up to be of 49-days age, the feeding schedule being shown in the left-handed front row in Table 3. Free intake of feed and water by every broiler was permitted. The stocking condition was as follows: During the period of from 0 to 14-days age, the broilers were reared in a window-less poultry house (15 to 20° C.), of which the floor was warmed with a floor heater, with 24-hours lighting, and the stocking density was 15 birds/m². During the period of from 15 to 49-days age, they were reared in an open poultry house (5 to 15° C.) with no heater, and the stocking density was 13 birds/m².

For comparison, day-old broiler chicks of the same type were fed in the same manner as above but according to the feeding schedule (left-handed last row in Table 3) not falling within the scope of the feeding method of the invention.

The broilers were thus reared under different conditions noted above, and the number of the broilers died during the rearing period was counted. The died broilers were subjected to a postmortem examination to know the cause of the death, on the basis of which they were classified into those having ascites and those not having it. After the rearing period, the number of deaths from ascites, the number of those not from ascites and the number of total deaths in each group were obtained. The body weight of each survival broiler was measured, and the mean body weight of each group was obtained. The feeding test was repeated four times in all for each group (totaling 200 birds/group), and the data obtained are shown in Table 3, in which the number of deaths indicates the total of the four tests (200 birds/group), and the body weight indicates the mean value of the four tests (200 birds/group).

TABLE 3

| | | Feed Sample | | | | Number of Deaths (birds) | | | Mean Body |
|---|---|---|---|---|---|---|---|---|---|
| | | 0 to 14-days age | 15 to 21-days age | 22 to 35-days age | 36 to 49-days age | Total | Ascites | Others | Weight (g) |
| Examples | 6 | A | D-5 | D | D | 17 | 14 | 3 | 2609 |
| | 7 | A | D-10 | D | D | 18 | 14 | 4 | 2601 |
| | 8 | A | D-15 | D | D | 14 | 11 | 3 | 2611 |
| | 9 | A | D-20 | D | D | 14 | 10 | 4 | 2607 |
| Comparative Examples | 6 | A | D | D | D | 36 | 27 | 9 | 2591 |
| | 7 | A-20 | D | D | D | 30 | 26 | 4 | 2585 |
| | 8 | A | D | D | D-20 | 33 | 23 | 10 | 2596 |

Examples 10 to 15

Plural groups of day-old broiler chicks (breed: Ross (male), day-old, mean body weight of 40 g), each group being composed of 50 birds, were fed with each of the feed compositions prepared above, in a floor feeding manner, up to be of 49-days age, the feeding schedule being shown in the left-handed front row in Table 4. Free intake of feed and water by every broiler was permitted. The amount of the feed having been consumed by the broilers was recorded during the rearing period. The rearing condition was completely the same as that in Examples 6 to 9 and Comparative Examples 6 to 8.

For comparison, day-old broiler chicks of the same type were fed in the same manner as above but according to the feeding schedule (left-handed last row in Table 4) not falling within the scope of the feeding method of the invention.

The broilers were thus reared under different conditions noted above, and the number of the broilers died during the rearing period was counted. After the rearing period, the body weight of each survival broiler was measured, and the mean body weight of each group was obtained. The feeding test was repeated four times in all for each group (totaling 200 birds/group), and the data obtained are shown in Table 4, in which the number of deaths indicates the total of the four tests (200 birds/group), and the body weight indicates the mean value of the four tests (200 birds/group) From the number of deaths, obtained was the growth rate (=100× (200−deaths)/200). In addition, from the feed intake data having been recorded during the rearing period, obtained was the feed intake per body weight gain, which indicates the feed conversion rate of the broilers. Based on those values obtained herein, the production score was calculated according to the following equation. The data thus obtained are shown in Table 4.

$$\text{Production score} = [(\text{mean body weight} \times \text{growth rate}/1000)/(\text{rearing period (days)} \times \text{feed conversion rate})] \times 100$$

The production score is a factor employed herein for evaluating the productivity of broilers. It shall be said that a higher production score means a higher productivity.

Examples 16, 17

Plural groups of day-old broiler chicks (breed: Ross (male), day-old, mean body weight of 40 g), each group being composed of 50 birds, were fed with each of the feed compositions prepared above, in a floor feeding manner, up to be of 49-days age, the feeding schedule being shown in the left-handed front row in Table 5. Free intake of feed and water by every broiler was permitted. The amount of the feed having been consumed by the broilers was recorded during the rearing period. The rearing condition was completely the same as that in Examples 6 to 9 and Comparative Examples 6 to 8.

For comparison, day-old broiler chicks of the same type were fed in the same manner as above, but using the feed composition not falling within the scope of the invention according to the feeding schedule (left-handed last row in Table 5) not falling within the scope of the invention.

The broilers were thus reared under different conditions noted above, and the number of the broilers died during the rearing period was counted. After the rearing period, the body weight of each survival broiler was measured, and the mean body weight of each group was obtained. The feeding test was repeated four times in all for each group (totaling 200 birds/group), and the data obtained are shown in Table 5, in which the number of deaths indicates the total of the four tests (200 birds/group), and the body weight indicates the mean value of the four tests (200 birds/group) the number of deaths, obtained was the r raising rate (=100× (200−deaths)/200). In addition, from the feed intake having been recorded during the rearing period, obtained the feed intake per body weight gain, which indicates the conversion rate of the broilers. Based on those values obtained herein, the production score was calculated in the manner as above. The data thus obtained are shown in Table 5.

TABLE 4

| | | Feed Sample | | | | | Feed | | | |
| --- | --- | --- | --- | --- | --- | --- | --- | --- | --- | --- |
| | | 0 to 14-days age | 15 to 21-days age | 22 to 28-days age | 29 to 35-days age | 36 to 49-days age | Mean Body Weight (g) | Raising Rate (%) | Conversion Rate (%) | Production Score |
| Examples | 10 | A | D-10 | D | D | D | 2617 | 94.0 | 2.09 | 240.0 |
| | 11 | A | D-10 | D-10 | D | D | 2612 | 92.5 | 2.12 | 232.6 |
| | 12 | A | D-10 | D-10 | D-10 | D | 2617 | 94.5 | 2.08 | 242.6 |
| | 13 | A | D | D-10 | D | D | 2599 | 90.5 | 2.13 | 225.4 |
| | 14 | A | D | D-10 | D-10 | D | 2605 | 93.5 | 2.11 | 235.6 |
| | 15 | A | D | D | D-10 | D | 2594 | 92.0 | 2.17 | 224.4 |
| Comp. Examples | 9 | A | D | D | D | D | 2605 | 82.0 | 2.37 | 183.9 |
| | 10 | A-10 | D | D | D | D | 2597 | 83.5 | 2.34 | 189.1 |
| | 11 | A | D | D | D | D-10 | 2584 | 85.0 | 2.29 | 195.7 |
| | 12 | A-10 | D | D | D | D-10 | 2588 | 86.0 | 2.32 | 195.8 |

TABLE 5

| | Feed Sample | | | Feed | | | |
| --- | --- | --- | --- | --- | --- | --- | --- |
| | 0 to 14-days age | 15 to 35-days age | 36 to 49-days age | Mean Body Weight (g) | Raising Rate (%) | Conversion Rate (%) | Production Score |
| Example 16 | A | D-15 | D | 2618 | 94.0 | 2.08 | 241.5 |
| Example 17 | A | D-15 | D (M) | 2588 | 96.5 | 2.13 | 239.3 |
| Comp. Example 13 | A | D-15 (M) | D | 2547 | 90.0 | 2.29 | 204.3 |
| Comp. Example 14 | A | D (M) | D (M) | 2604 | 82.0 | 2.37 | 183.9 |

Examples 18, 19

Plural groups of day-old broiler chicks (breed: Ross (male), day-old, mean body weight of 40 g), each group being composed of 50 birds, were fed with each of the feed compositions prepared above, in a floor feeding manner, up to be of 49-days age, the feeding schedule being shown in the left-handed front row in Table 6. Free intake of feed and water by every broiler was permitted. The amount of the feed having been consumed by the broilers was recorded during the rearing period. The rearing condition was completely the same as that in Examples 6 to 9 and Comparative Examples 6 to 8.

For comparison, day-old broiler chicks of the same type were fed in the same manner as above, but using the feed composition not falling within the scope of the invention according to the feeding schedule (left-handed last row in Table 6) not falling within the scope of the invention.

The broilers were thus reared under different conditions noted above, and the number of the broilers died during the rearing period was counted. After the rearing period, the body weight of each survival broiler was measured, and the mean body weight of each group was obtained. The feeding test was repeated four times in all for each group (totaling 200 birds/group), and the data obtained are shown in Table 6, in which the number of deaths indicates the total of the four tests (200 birds/group), and the body weight indicates the mean value of the four tests (200 birds/group). From the number of deaths, obtained was the r raising rate (=100× (200−deaths)/200). In addition, from the feed intake having been recorded during the rearing period, obtained the feed intake per body weight gain, which indicates the conversion rate of the broilers. Based on those values obtained, the production score was calculated in the manner as above. The data thus obtained are shown in Table 6.

From those data, it is obvious that feeding broilers with the feed composition of the invention makes it possible to well prevent the broilers from having ascites and to increase the raising rate and the growth rate of the broilers, thereby increasing the productivity in broiler raising. In addition, it is also obvious that, in the feeding method for broilers of the invention, the feed composition of the invention is effectively taken by broilers, and that the method ensures high productivity in broiler raising.

INDUSTRIAL APPLICABILITY

Feeding the feed composition of the invention to broilers makes it possible to well prevent the broilers from having ascites and to increase the growth rate of the broilers, whereby the raising rate of the broilers is increased and the rearing period thereof is shortened. According to the feeding method for broilers of the invention, broilers can effectively take the feed composition of the invention, whereby the productivity in broiler raising is much increased.

What is claimed is:

1. A feeding method for broilers, which comprises feeding a feed composition which has a metabolizable energy value of not smaller than 3150 kcal/kg and contains coenzyme Q and which has been pelletized into pellets, to broilers for 7 days or longer while the broilers being fed therewith are of 10 to 35-days age.

2. The method of claim 1, wherein the broilers are fed for 14 days or longer.

3. The method of claim 1, wherein the broilers are of 15 to 28-days age.

4. The method of claim 2, wherein the broilers are of 15 to 28-days age.

5. A feeding method for broilers, which comprises feeding a feed composition which has a metabolizable energy value of not smaller than 3150 kcal/kg and contains coenzyme Q, wherein the coenzyme Q content is from 0.0005 to 0.0003% by weight of the total amount of the composition, and which has been pelletized into pellets, to broilers for 7 days or longer while the broilers being fed therewith are of 10–35 days in age.

6. The method of claim 5, wherein the broilers are fed for 14 days or longer.

TABLE 6

| | Feed Sample | | | Feed | | | |
| --- | --- | --- | --- | --- | --- | --- | --- |
| | 0 to 14-days age | 15 to 35-days age | 36 to 49-days age | Mean Body Weight (g) | Raising Rate (%) | Conversion Rate (%) | Production Score |
| Example 18 | A | D-20 | D | 2619 | 94.5 | 2.09 | 241.7 |
| Example 19 | A | E-30 | D | 2825 | 91.5 | 2.14 | 246.5 |
| Comp. Example 16 | A | B-20 | B | 2522 | 95.0 | 2.32 | 210.8 |
| Comp. Example 17 | A | C-30 | C | 2554 | 94.5 | 2.26 | 217.9 |

7. The method of claim 5, wherein the broilers are of 15 to 28-days age.

8. The method of claim 6, wherein the broilers are of 15 to 28-days age.

* * * * *